(12) United States Patent
Shekunov et al.

(10) Patent No.: US 6,986,846 B2
(45) Date of Patent: Jan. 17, 2006

(54) METHOD AND APPARATUS FOR ENHANCED SIZE REDUCTION OF PARTICLES USING SUPERCRITICAL FLUID LIQUEFACTION OF MATERIALS

(75) Inventors: Boris Y. Shekunov, Aurora, OH (US); Pratibhash Chattopadhyay, North Royalton, OH (US); Jeffrey S. Seitzinger, Broadview Heights, OH (US)

(73) Assignee: Ferro Corporation, Cleveland, OH (US)

( * ) Notice: Subject to any disclaimer, the term of this patent is extended or adjusted under 35 U.S.C. 154(b) by 0 days.

(21) Appl. No.: 10/932,559

(22) Filed: Sep. 2, 2004

(65) Prior Publication Data

US 2005/0082701 A1 Apr. 21, 2005

Related U.S. Application Data

(60) Provisional application No. 60/499,499, filed on Sep. 2, 2003.

(51) Int. Cl.
*B01D 11/02* (2006.01)
*A61K 9/14* (2006.01)

(52) U.S. Cl. .......................... 210/634; 264/5; 366/102; 366/341; 366/348; 424/489

(58) Field of Classification Search ................ 210/511, 210/634, 639, 774; 424/489–491; 366/152.1, 366/336–341, 101, 102, 348; 264/5, 6, 11, 264/12; 239/8–10; 516/135, 195
See application file for complete search history.

(56) References Cited

U.S. PATENT DOCUMENTS

| | | | | |
|---|---|---|---|---|
| 4,923,720 A | * | 5/1990 | Lee et al. ................... | 427/422 |
| 5,106,659 A | * | 4/1992 | Hastings et al. ......... | 427/427.4 |
| 5,290,827 A | | 3/1994 | Shine | |
| 5,399,597 A | | 3/1995 | Mandel et al. | |
| 5,464,283 A | * | 11/1995 | Davis ...................... | 366/152.1 |
| 5,639,441 A | * | 6/1997 | Sievers et al. ............... | 424/9.3 |
| 5,766,637 A | | 6/1998 | Shine et al. | |
| 6,056,791 A | * | 5/2000 | Weidner et al. ........... | 23/295 R |
| 6,372,260 B1 | * | 4/2002 | Andersson et al. ......... | 424/501 |

* cited by examiner

*Primary Examiner*—Joseph Drodge
(74) *Attorney, Agent, or Firm*—Rankin, Hill, Porter & Clark LLP

(57) ABSTRACT

The present invention provides a method and an apparatus for forming particles using supercritical fluid. The method includes the steps of mixing a load material with a first flow of a supercritical fluid in a first mixing chamber having a primary mixing device disposed therein to form a melt, transferring the melt from the first mixing chamber to a second mixing chamber having a secondary mixing device disposed therein, mixing the melt with a second flow of the supercritical fluid in the second mixing chamber to form a lower viscosity melt, expanding the lower viscosity melt across a pressure drop into an expansion chamber that is at a pressure below the critical pressure of the supercritical fluid to convert the supercritical fluid to a gas and thereby precipitate the load material in the form of particles.

10 Claims, 2 Drawing Sheets

METHOD AND APPARATUS FOR ENHANCED SIZE REDUCTION OF PARTICLES USING SUPERCRITICAL FLUID LIQUEFACTION OF MATERIALS

BACKGROUND OF THE INVENTION

1. Field of Invention

The present invention relates to an apparatus and a method for producing particles using supercritical fluid and, more particularly, to an apparatus and a method for producing particles using a supercritical fluid and a secondary mixing assembly.

2. Description of Related Art

Particles having very small diameters and a narrow range of particle sizes are desired for a variety of end-use applications such as, for example in the production of pharmaceutical compositions. Several processes have been developed over the years to produce single-component and multi-component (i.e., composite) particles utilizing the enhanced mass-transfer properties and generally benign nature of supercritical fluids, near-critical fluids and compressed gases. Unfortunately, it has been very difficult to obtain small sized particles (diameters less than 100 $\mu$m) with a narrow particle size distribution using such processes.

One such supercritical fluid processing technique is known in the art as Particles from Gas-Saturated Solutions (PGSS). In the conventional PGSS technique, a compound or a mixture of compounds is plasticized with a supercritical fluid to form a plasticized mass or "melt" that is then expanded across a pressure drop. The rapid decrease in pressure causes the supercritical fluid to change into a gas phase, which results in supersaturation and ultimately precipitation of the compound or mixture of compounds as particles.

Particle agglomeration is frequently problematic in conventional PGSS processing. During particle formation, bridges can form between growing particles, which can lead to large differences in particle size and wide particle size distributions. Furthermore, particles produced by conventional PGSS processing techniques tend to exhibit a broad size distribution in sizes above 100 $\mu$m and tend to be non-uniform (i.e., irregular) in shape.

Another problem typically associated with the conventional PGSS process is that mixtures of compounds tend to separate as they pass across the pressure drop. The separation phenomenon can make it difficult to produce uniform composite particles, and can actually result in the production of an undesirable blend of particles that are formed of one material or the other, but not both materials. Homogeneous composite polymer/drug micro-spheres and uniform coated particles are particularly difficult to produce using the conventional PGSS process.

The particle agglomeration problem typically encountered with the PGSS process is exacerbated when the melt comprises one or more compounds that exhibit a relatively high melt viscosity. Polymers, which are often used as carriers or excipients for pharmaceutical compositions, tend exhibit a relatively high viscosity in such melts. Because of the undesirable viscosity and concentration of the polymer relative to the supercritical fluid used to form the melt, efficient particle dispersion is difficult to obtain. Furthermore, the process is often plagued with nozzle clogging and poor particle coating efficiency. Demixing and poor wetting between the carrier and biologically active agents further reduces the coating efficiency and can lead to an undesirable non-homogeneous particle coating.

BRIEF SUMMARY OF THE INVENTION

The present invention provides an apparatus and a method for producing particles using supercritical fluid. The apparatus and method provide enhanced mixing between the supercritical fluid and a load material that comprises on or more compounds to be processed into particles. The apparatus according to the invention comprises a first mixing chamber and a second mixing chamber that is in fluid communication with the first mixing chamber. A primary mixing device, which is preferably a rotating mechanical agitator, is disposed in the first mixing chamber for mixing the load material and a supercritical fluid, near-critical fluid or compressed gas to form a melt. A secondary mixing device, which is preferably a static mixing element, is disposed in the second mixing chamber for mixing the melt with a fresh supply of supercritical fluid, near-critical fluid or a compressed gas that enters the second mixing chamber through an inlet. The pressure in the first mixing chamber is preferably higher than the pressure in the second mixing chamber, which facilitates material transfer from the first mixing chamber to the second mixing chamber. The apparatus according to the invention further comprises an expansion chamber that is in fluid communication with the second mixing chamber.

In accordance with the method of the invention, a melt is formed in a first mixing chamber. The melt comprises a load material and a supercritical fluid, a near-critical fluid and/or a compressed gas. In the preferred embodiment of the invention, supercritical carbon dioxide is used. The melt passes from the first mixing chamber into the second mixing chamber and is contacted with a stream of fresh supercritical fluid, near-critical fluid or compressed gas, which mixes with and reduces the viscosity of the melt as it passes through the secondary mixing device. The lower viscosity melt exits the second mixing chamber and is expanded across a pressure drop into an expansion chamber. Expansion of the lower viscosity melt causes the supercritical fluid, near-critical fluid or compressed gas to flash or convert to a gas phase, causing supersaturation of the melt and precipitation of the load material in the form of particles. The particles will generally exhibit a small size (mean diameters less than 100 $\mu$m) and a narrow particle size distribution. If desired, the resultant particles can be milled or otherwise further processed. The apparatus and method of the invention are particularly suitable for use in producing composite particles, for example, polymer encapsulated drug particles.

In a second embodiment of the invention, one or more additional compounds are combined and mixed with the melt in the second mixing chamber. The additional compounds are preferably in liquid form, either neat or by virtue of having been dissolved or plasticized with a solvent or supercritical fluid to facilitate mixing with the melt. It is thus possible to mix biologically active compounds with lower viscosity polymer melts.

In all embodiments of the invention, the lower viscosity melt is directed from the second mixing chamber into an expansion chamber, preferably by spraying through a nozzle having one or more fine apertures. The rapid decrease in pressure causes the supercritical fluid, near-critical fluid and/or compressed gas to expand and flash or convert to a gas phase. The decrease in concentration of the supercritical fluid, near-critical fluid and/or compressed gas in the melt results in supersaturation and then precipitation of fine particles. Adiabatic expansion also results in substantial cooling. As a result, the melt solidifies in the form of fine particles, which are typically porous. Diffusion of the supercritical fluid, near-critical fluid and/or compressed gas from the melt due to temperature and pressure reduction further reduces particle size and may enhance the porosity of the particles.

The higher concentration of supercritical fluid and lower viscosity of the melt produced through the use of the secondary mixing device in the second mixing chamber advantageously facilitates the production of particles that a smaller size and a narrower particle size distribution than can be achieved using conventional PGSS processing techniques. Simply increasing the amount of supercritical fluid in a mechanically agitated mixing chamber does not result in the advantages provided by the present invention.

The foregoing and other features of the invention are hereinafter more fully described and particularly pointed out in the claims, the following description setting forth in detail certain illustrative embodiments of the invention, these being indicative, however, of but a few of the various ways in which the principles of the present invention may be employed.

DETAILED DESCRIPTION OF THE INVENTION

Figure 1:
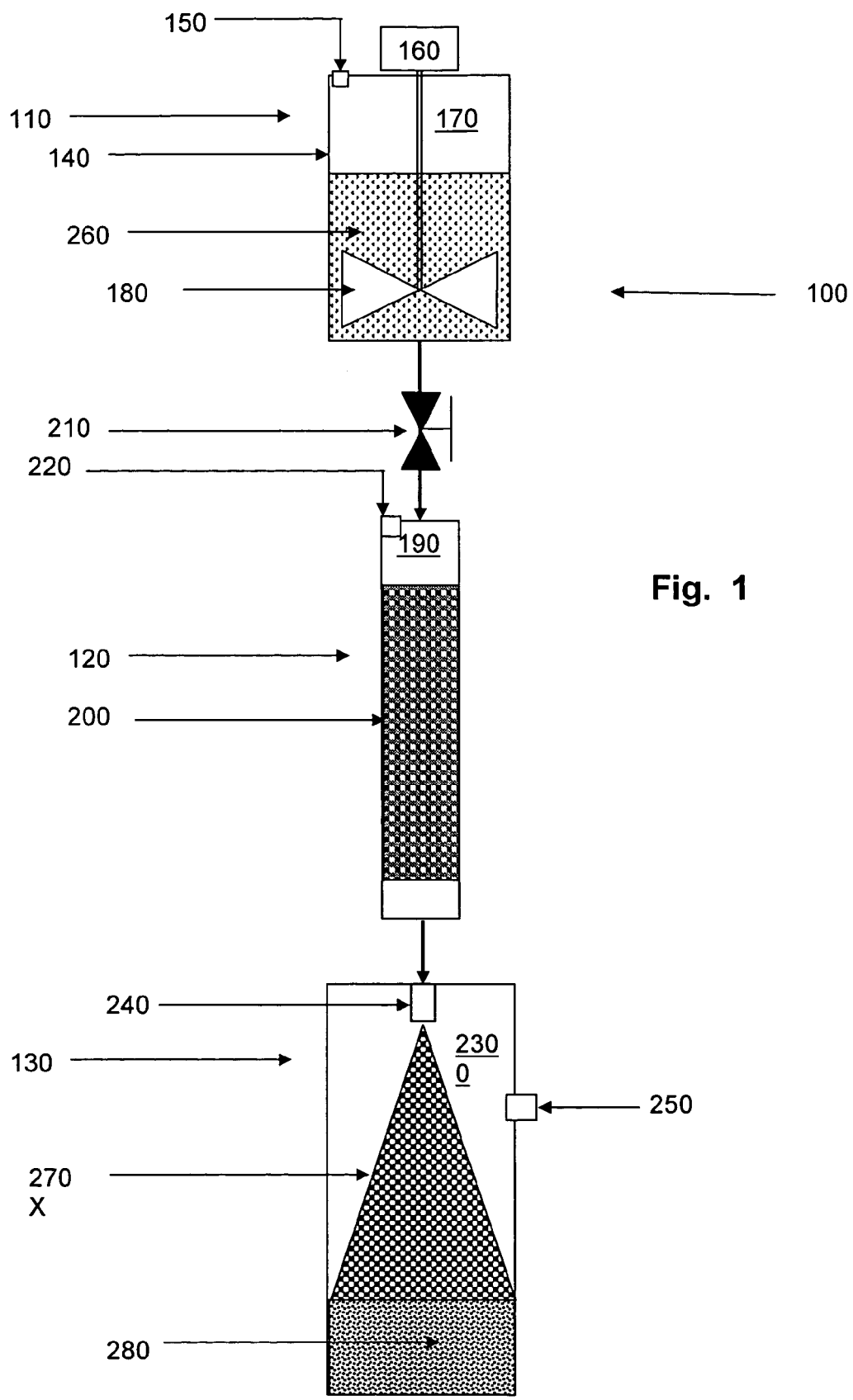
FIG. 1 is a schematic drawing of an apparatus according to the invention.
Figure 2:
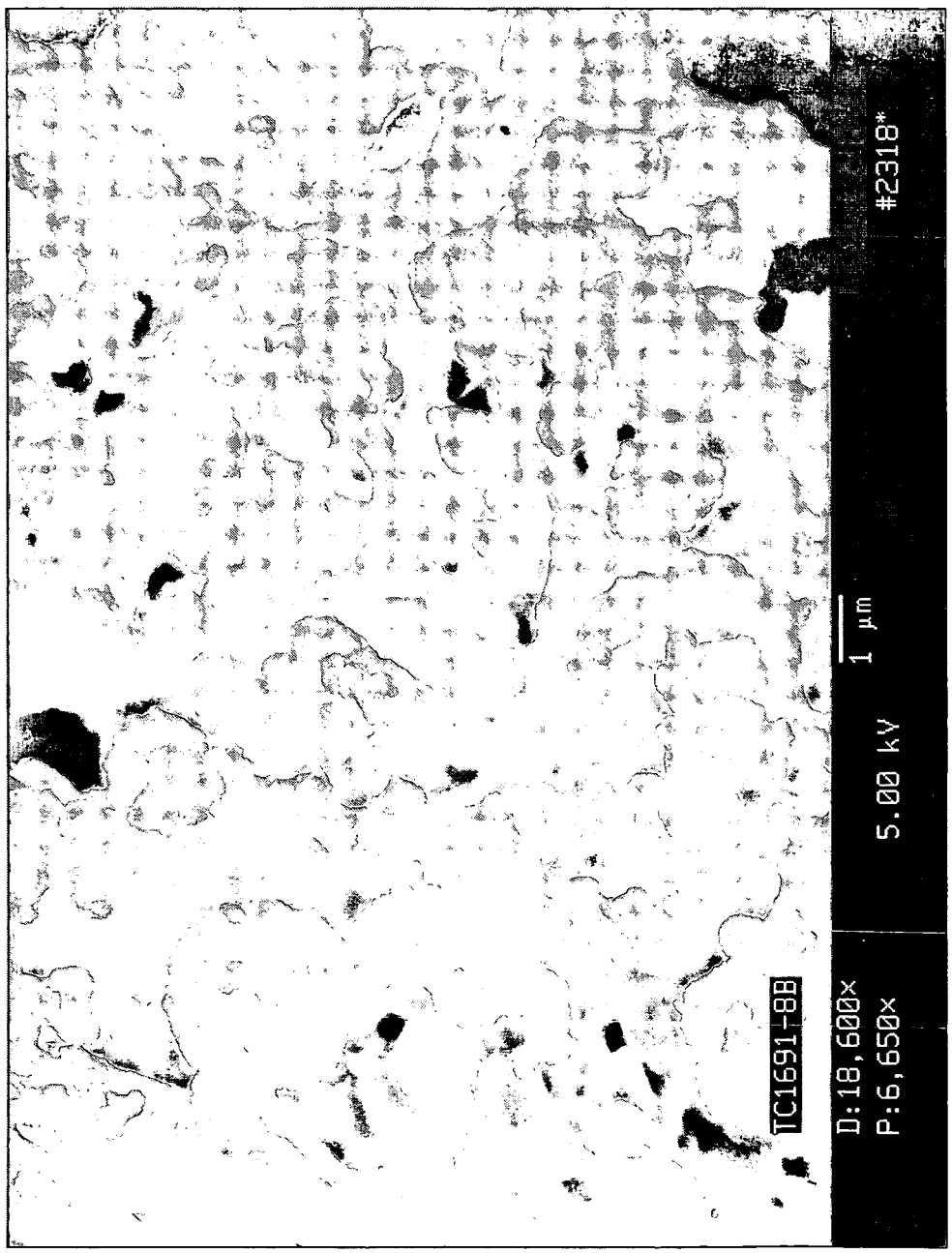
FIG. 2 is a scanning electron microscope (SEM) micrograph of particles produced in Example 1.

With reference to FIG. 1, an apparatus 100 according to the invention generally comprises a first mixing assembly 110, a second mixing assembly 120 and an expansion assembly 130. The first mixing assembly 110 comprises a first mixing vessel 140, an optional solvent pump (not shown), a supercritical fluid pump (not shown) that supplies supercritical fluid into the mixing vessel 140 through an inlet 150, a thermostat (not shown) and a first or primary mixing device.

The first or primary mixing device may consist of a static mixer or a dynamic mixer or a combination of both. Static mixers are difficult to use in the first mixing chamber when the load material consists of powdered materials. In such a circumstance, a mechanical agitator must be used. Accordingly, the first or primary mixing device preferably comprises a rotating mechanical agitator driven by a motor 160.

The first mixing vessel 140 is preferably tubular and has first and second ends that are spaced axially apart. The first mixing vessel 140 has an inner surface that defines a mixing chamber 170. The pressure in the mixing chamber 170 is maintained constant during operation. The first mixing assembly 110 includes means for charging the mixing chamber 170 with a load material.

A preferred lab-scale supercritical fluid pump is a P-200 high-pressure reciprocating pump commercially available from Thar Technologies, Inc. of Pittsburgh, Pa. Suitable alternative pumps include diaphragm pumps and air-actuated pumps that provide a continuous flow of supercritical fluid. The high-pressure pump preferably comes factory-equipped with a burst-type rupture disc, manufactured by Fike Inc. of Blue Springs, Mo., which is plumbed into a pressure relief system. The supercritical fluid pump preferably supplies supercritical fluid through both a surge tank and a metering valve so as produce a pulse-free flow.

When the primary mixing device comprises a rotating mechanical agitator driven by a motor 160, a shaft extends from the motor 160 through the second end of the first mixing vessel 110 into the first mixing chamber 170. A rotor 180 is disposed at a distal end of the shaft and located in the chamber 170. The mixing rate is controlled by the rotation speed and geometry (type and diameter) of the rotor 180. The rotor 180 is preferably a propeller-shaped two-bladed mixer. Other supplemental mechanical mixing elements such as baffles, rotors, turbines, shear-mixers can also be disposed within the first mixing chamber 170, if desired.

The second mixing assembly 120 includes interior walls that define a second mixing chamber 190. A secondary mixing device is disposed within the second mixing chamber 190. The second mixing assembly 120 also preferably comprises a thermostat (not shown). The second mixing chamber 190 is preferably cylindrical and has first and second ends that are spaced axially apart.

In the presently most preferred embodiment of the invention, the secondary mixing device comprises a static mixer 200. Static mixers having different geometries are well known in the art. It will be appreciated that the secondary mixing device can comprise a static mixer alone, a dynamic mixing device alone, or a combination of both. Examples of suitable dynamic mixers are high-shear rotor-stator mixers, rotating turbines and helicoidal (spiral) mixers.

The second mixing assembly 120 is in fluid communication with the first mixing assembly 110. A release valve 210 is preferably disposed between the first mixing assembly 120 and the second mixing assembly 120. The pressure in the second mixing chamber 190 is maintained at a reduced pressure relative to the pressure in the first mixing chamber 170 to facilitate flow of material from the first mixing chamber 170 to the second mixing chamber 190 through the release valve 210. The second mixing chamber 190 is preferably in fluid communication with a supercritical fluid pump (not shown), which may be the same as or different than the supercritical fluid pump in communication with the first mixing chamber 170. The supercritical fluid pump supplied supercritical fluid into the second mixing chamber 190 through an inlet 220.

As noted, preferably one or more static mixing elements 200 are disposed within the second mixing chamber 190. Suitable static mixing elements are commercially available from Koch Enterprise, Inc., which is now owned by Sulzer Chemtech USA, Inc. of Pasadena, Tex. If desired, one or more dynamic mixing elements such as high-shear, rotor-stator mixers, turbines and helicoidal (spiral) mixers, can also be disposed in the second mixing chamber and driven by a motor and a shaft. The secondary mixing device helps mix the melt transferred from the first mixing chamber 170 with the fresh supercritical fluid pumped into the second mixing chamber 190, which forms a lower viscosity melt. The flow of supercritical fluid into the second mixing chamber 190 also assists the flow of the lower viscosity melt through the static mixing element 200. The static mixing element 200 preferably breaks the melt into relatively finer droplets, which can intimately and efficiently mix with the melt.

Backpressure regulators can be used to maintain the desired pressures in the first and second mixing chambers during operation. A particularly suitable backpressure regulator is a model 26–1700, which is commercially available from Tescom, USA of Elk River, Minn.

A thermostat communicates with heating elements (not shown) that are preferably located proximate to the first mixing assembly 110, the second mixing assembly 120, the expansion assembly 140 and the release valve 210. A controller communicates with and controls the optional solvent pump, the supercritical fluid pump or pumps, the thermostat, the motor 160 of the mixer apparatus, the backpressure regulators and the release valves. Suitable controllers are interchangeable and are commercially available.

The expansion assembly 140 comprises a vessel having an inner surface that defines an expansion chamber 230. The lower viscosity melt passes from the second mixing vessel 190 into the expansion chamber 230 through a nozzle 240 provided with one or more apertures having a very small diameter. The expansion chamber 230 is maintained at a substantially lower pressure than the second mixing chamber 190, which is below the critical pressure of the supercritical fluid. Thus, upon passing through the nozzle 240, the supercritical fluid flashes and changes phase to become a gas, which can be removed through a vent 250. The phase change of the supercritical fluid to a gas results in the precipitation of the load material in the melt in the form of fine particles. One or more filters can be used to trap or collect the precipitated particles.

In accordance with the method of the invention, the first mixing vessel 170 is charged with a quantity of load material. The load material can be a single compound or a mixture of two or more compounds such as a biologically active material and a coating agent. Alternatively, the load material can be or can include a biodegradable polymer, medicinal agent, pigment, toxin, insecticide, viral material, diagnostic aid, agricultural chemical, nutritional material, protein, alkyloid, peptide, animal and/or plant extract, dye, explosive, paint, polymer precursor, cosmetic, antigen, enzyme, catalyst, nucleic acid, zeolite, hormone gastrointestinal acid suppressant, surfactant, dispersing aid, and combinations thereof. The load material can further include one or more additional materials such as, for example, a carrier, polymer, filler, disintegrant, binder, solubilizer, excipient, surfactant and combinations thereof. A preferred load material is a combination of a biologically active material and a biodegradable polymer such as, for example, a polysaccharide, polyester, polyether, polyanhydride, polyglycolide (PLGA), polylactic acid (PLA), polycaprolactone (PCL), polyethylene glycol (PEG) or a polypeptide.

An optional solvent that is a liquid below its critical temperature and pressure may also be introduced with the load material. Solvents can be used to further lower the viscosity of the melt during operation. Suitable solvents include, for example, water, alcohol, toluene, ethyl acetate, methyl chloride, methylene chloride, dimethyl sulfoxide (DMSO), dimethyl formamide (DMF), other organic or inorganic solvents, and combinations thereof. The solvent may have a solute dissolved therein. Thus, solvent is herein defined to include a solution of solvent and solute. Solvent is also defined to include an emulsion or a dispersion of material suspended in the solvent.

Once the load material is charged to the first mixing chamber, the supercritical fluid pump is activated to supply a quantity of supercritical fluid through a surge tank, a metering valve and into the first mixing chamber. The supercritical fluid contacts the load material under mixing conditions to form a melt 260. The addition of the supercritical fluid by the supercritical fluid pump increases the pressure in the first mixing chamber. The controller maintains the pressure and temperature at predetermined levels. Preferably, the controller maintains the temperature and pressure such that the supercritical fluid is maintained in a supercritical state.

The supercritical fluid is preferably supercritical carbon dioxide ("$CO_2$"). Suitable alternative supercritical fluids include water, nitrous oxide, dimethylether, straight chain or branched C1–C6-alkanes, alkenes, alcohols, and combinations thereof. Preferable alkanes and alcohols include ethane, ethanol, propane, propanol, butane, butanol, isopropane, isopropanol, and the like. The supercritical fluid is chosen generally with reference to the ability of the supercritical fluid to plasticize the load material during a mixing and melt formation operation. Although use of a supercritical fluid such as supercritical carbon dioxide is presently most preferred, there may be instances where a near-critical fluid or a compressed or liquefied gas could be used instead of a supercritical fluid.

Once the supercritical fluid is introduced into the first mixing vessel, the motor of the mixer apparatus is engaged to rotate the shaft and the rotor. If an optional solvent is desired, a solvent pump can be engaged to supply solvent into the first mixing chamber. The rotor mixes the supercritical fluid, the optional solvent and the load material until a substantially uniform melt 260 is achieved. The term "melt" means that the load material is solvated or sufficiently plasticized by the supercritical fluid such that it behaves as a fluid or semi-fluid and thus can be processed accordingly.

If desired, in cases where the load material is charged into the first mixing chamber as a solution, excess supercritical fluid can be circulated through the first mixing chamber to remove supercritical fluid soluble solvents from the first mixing chamber. Alternatively, the solvent can remain in the melt, or can be removed during subsequent process steps.

Once the melt 260 is sufficiently formed in the first mixing chamber, the backpressure regulator and the release valve are adjusted by the controller to transfer the melt from the first mixing chamber to the second mixing chamber. The pressure in the first mixing chamber can be adjusted such that it is greater in the first mixing chamber than in the second mixing chamber, which means that when the release valve is opened, the melt flows from the first mixing chamber to the second mixing chamber. The pressure inside the second mixing chamber can be effectively maintained at a constant predetermined pressure using a backpressure regulator.

A stream of fresh supercritical fluid such as supercritical carbon dioxide is also introduced into the second mixing chamber using a supercritical fluid pump. The flow of the supercritical fluid, and optionally gravity, pushes or drives the melt through the static mixers disposed within the second mixing chamber. The fresh supercritical fluid blends and mixes with the melt forming a lower viscosity melt.

The expansion chamber, which is in fluid communication with the second mixing chamber, is maintained at a temperature and pressure below the critical point of the supercritical fluid. Most preferably, the expansion chamber is maintained at or near ambient temperature and atmospheric pressure. The lower viscosity melt is expands across a pressure drop through the nozzle into the expansion chamber. The pressure reduction causes the supercritical fluid in the lower viscosity melt to flash to a gaseous phase. The loss of supercritical fluid from the melt increases the melt point and/or glass transition temperature of the load material in the melt, decreases the temperature of the load material in the melt, and expands to increase the volume of the load material in the melt. The melt rapidly solidifies into particles of load material 270, which can be collected using a filter 280 or other collection means.

As noted hereinabove, the phase change of the supercritical fluid from liquid to gas reduces the localized temperature of materials adjacent to the expansion location (i.e., at the nozzle outlet), which is sometimes called adiabatic expansion. If a nozzle heater is present, the nozzle can be heated to reduce the level of solvent in the particles, and to affect particle characteristics, such as size and morphology. If no heater is used, a temperature reduction that normally accompanies such an expansion can further decrease particle size based on cryo-fracturing of the forming particles. Further, a portion of the supercritical fluid may crystallize in response to the temperature reduction. Whether a portion of the supercritical fluid crystallizes is determined by factors such as the selection of supercritical fluid, and the temperature and pressure of the expansion chamber during operation.

If any materials were dissolved, and/or suspended in the supercritical fluid, the dissolved or suspended materials precipitate or solidify during the expansion and phase change of the supercritical fluid. In addition, any other materials that were added to the melt during mixing and formation of the melt are also formed into the particles as a coating, core, microsphere, microcapsules, etc. The particles thus form composite particles that collect in the expansion chamber. Rather than discrete particles, the process parameters can be adjusted so that the expanded material precipitates as a suspension, a foam, a web, or a gel, or the particles characteristics can be modified such that the particles have different surface profiles or morphologies, for example sphere, rod, or other basic geometric shape, and can be discrete or can be grouped or agglomerated. The particles can also form a suspension in the solvent if the solvent is not removed during the mixing or the expansion step.

The following examples are intended only to illustrate the invention and should not be construed as imposing limitations upon the claims. The chemicals used in the following examples can be obtained from a variety of chemical suppliers including, but not limited to, Alpha Aeser, Inc. of Ward Hill, Mass. and Spectrum Chemical Mfg. Corp. of Gardena, Calif.

EXAMPLE 1

5.17 g of polycaprolactone (PCL) and 0.06 g of trypsinogen were charged to a first mixing chamber of an apparatus configured as shown in FIG. 1. The first mixing chamber had a volume of 100 ml and had a diameter of 32 mm. The chamber was pressurized with carbon dioxide to a pressure of 30 MPa and heated to a temperature of 321K. The carbon dioxide became supercritical. The contents of the first mixing chamber were mixed together using a mixing blade that rotated at a constant speed of 1280 rpm. Mixing continued for 150 minutes. A PCL/trypsinogen melt was formed in the first mixing chamber.

The PCL/trypsinogen melt was flowed from the first mixing chamber through a valve and then through a nozzle into a second mixing chamber containing a static mixing assembly. The nozzle had an aperture with a diameter of 760 μm. A 200 g/min flow of fresh carbon dioxide at 25–27 MPa was flowed into the second mixing chamber through a carbon dioxide inlet. The PCL/trypsinogen melt mixed with the fresh carbon dioxide in the static mixing assembly and thereby formed a lower viscosity melt mixture.

The lower viscosity melt mixture in the second mixing chamber was expanded across a pressure drop into an expansion chamber through a fine nozzle having an aperture with a 250 μm diameter. At least a portion of the supercritical carbon dioxide changed phase to become a gas thereby resulting in supersaturation of the PCL/trypsinogen melt, which precipitated into PCL/trypsinogen composite particles. The carbon dioxide gas was removed from the expansion chamber using a vent.Expansion of the lower viscosity melt mixture also resulted in a temperature reduction, which may have caused a portion of the carbon dioxide to change phase and become solid particles. However, any solid carbon dioxide particles that may have been collected in the expansion chamber with the PCL/trypsinogen composite particles would have ultimately been removed via sublimation. FIG. 2 shows a scanning electron micrograph of the PCL/trypsinogen composite particles, which had a mean particle diameter of 17.4 μm.

EXAMPLE 2

10 g of PCL was charged to the first mixing chamber of the apparatus as used in Example 1. The first mixing chamber was pressurized with carbon dioxide to a pressure of 30 MPa and heated to a temperature of 343K. The carbon dioxide became supercritical. The PCL and supercritical carbon dioxide were mixed together using a mixing blade that rotated at a constant speed of 1200 rpm. Mixing continued for 150 minutes. A PCL melt was formed.

The PCL melt flowed from the first mixing chamber into the second mixing chamber containing the static mixing assembly. A 200 g/min flow of fresh carbon dioxide at 25–27 MPa was flowed into the second mixing chamber and mixed with the PCL melt to form a lower viscosity melt.

The lower viscosity melt flowed across a pressure drop from the second mixing chamber into the expansion chamber through a fine silica nozzle having an aperture with 50 μm diameter. At least a portion of the supercritical carbon dioxide changed phase and become a gas thereby resulting in supersaturation of the PCL melt, which precipitated into PCL particles. The carbon dioxide gas was removed from the expansion chamber using a vent. Expansion of the lower viscosity melt also resulted in a temperature reduction, which may have caused a portion of the carbon dioxide to change phase and become solid particles. However, any solid carbon dioxide particles that may have been collected in the expansion chamber with the PCL particles would have ultimately been removed via sublimation. The PCL particles collected in the expansion chamber had a mean particle diameter of 6.7 μm. Table 1 below lists detailed particle size measurement data for the PCL particles formed in Example 2.

TABLE 1

| Size (μm) | Frequency (%) | Over (%) |
|---|---|---|
| 22.80 | 0.00 | 0.00 |
| 19.90 | 0.28 | 0.00 |
| 17.38 | 0.80 | 0.28 |
| 15.17 | 1.89 | 1.08 |
| 13.25 | 3.72 | 2.97 |
| 11.56 | 6.16 | 6.69 |
| 10.10 | 8.77 | 12.85 |
| 8.816 | 10.83 | 21.62 |
| 7.697 | 11.92 | 32.45 |
| 6.720 | 11.84 | 44.37 |
| 5.867 | 10.77 | 56.21 |
| 5.122 | 9.40 | 66.98 |
| 4.472 | 7.76 | 76.38 |
| 3.905 | 5.64 | 84.14 |
| 3.409 | 4.00 | 89.78 |
| 2.976 | 2.62 | 93.78 |
| 2.599 | 1.59 | 96.40 |
| 2.269 | 0.92 | 97.99 |
| 1.981 | 0.48 | 98.91 |
| 1.729 | 0.25 | 99.39 |
| 1.510 | 0.12 | 99.64 |
| 1.318 | 0.00 | 99.76 |
| 1.151 | 0.00 | 99.76 |

TABLE 1-continued

| Size (μm) | Frequency (%) | Over (%) |
|---|---|---|
| 1.006 | 0.00 | 99.76 |
| 8.877 | 0.00 | 99.76 |
| 0.766 | 0.00 | 99.76 |
| 0.669 | 0.00 | 99.76 |
| 0.584 | 0.00 | 99.76 |
| 0.510 | 0.00 | 99.76 |
| 0.445 | 0.00 | 99.76 |
| 0.389 | 0.00 | 99.76 |
| 0.339 | 0.00 | 99.76 |
| 0.296 | 0.00 | 99.76 |
| 0.259 | 0.00 | 99.76 |
| 0.226 | 0.00 | 99.76 |
| 0.197 | 0.12 | 99.76 |
| 0.172 | 0.12 | 99.88 |
| 0.150 | 0.00 | 100.00 |

Additional advantages and modifications will readily occur to those skilled in the art. Therefore, the invention in its broader aspects is not limited to the specific details and illustrative examples shown and described herein. Accordingly, various modifications may be made without departing from the spirit or scope of the general inventive concept as defined by the appended claims and their equivalents.

What is claimed is:

1. A method of forming particles, the method comprising:
   mixing a load material with a first flow of a supercritical fluid in a first mixing chamber having a primary mixing device disposed therein to form a melt;
   transferring the melt from the first mixing chamber to a second mixing chamber having a secondary mixing device disposed therein;
   mixing the melt with a second flow of the supercritical fluid in the second mixing chamber to form a lower viscosity melt; and
   expanding the lower viscosity melt across a pressure drop into an expansion chamber that is at a pressure below the critical pressure of the supercritical fluid to convert the supercritical fluid to a gas and thereby precipitate the load material in the form of particles.

2. The method according to claim 1 wherein the primary mixing device comprises a mechanical agitator.

3. The method according to claim 1 wherein the secondary mixing device comprises a static mixing assembly.

4. The method according to claim 1 wherein the supercritical fluid comprises supercritical carbon dioxide.

5. The method according to claim 4 wherein the load material comprises a biologically active agent and a carrier.

6. The method according to claim 5 wherein the carrier is a biodegradable polymer.

7. The method according to claim 1 wherein the lower viscosity melt passes from the second mixing chamber into the expansion chamber through a nozzle having one or more small apertures formed therein.

8. The method according to claim 1 wherein the load material is dissolved in a solvent prior to being mixed with the supercritical fluid in the first mixing chamber.

9. The method according to claim 8 wherein the solvent is soluble in the supercritical fluid and is extracted from the first mixing chamber before the melt is transferred to the second mixing chamber.

10. The method according to claim 1 further comprising:
    contacting the melt with a solvent in the in the second mixing chamber; and
    recovering the particles in the expansion chamber as a suspension in the solvent.

* * * * *